United States Patent [19]

Heim et al.

[11] 4,316,380

[45] Feb. 23, 1982

[54] METHOD FOR DETERMINING THE ALCOHOL CONTENT IN BREATHING AIR

[75] Inventors: Ulrich Heim, Reinfeld; Eric Hecker, Stockelsdorf, both of Fed. Rep. of Germany

[73] Assignee: Drägerwerk Aktiengesellschaft, Fed. Rep. of Germany

[21] Appl. No.: 121,899

[22] Filed: Feb. 15, 1980

[30] Foreign Application Priority Data

Feb. 22, 1979 [DE] Fed. Rep. of Germany ....... 2906864

[51] Int. Cl.³ ............................................. G01N 21/00
[52] U.S. Cl. ....................................... 73/23; 128/719
[58] Field of Search ................. 73/23, 27 R, 421.5 R, 73/864.81, 864.85; 422/84, 232 E; 128/719; 340/632, 633, 634

[56] References Cited

U.S. PATENT DOCUMENTS 3,877,291 4/1975 Hoppesch et al. ................. 73/27 R
4,090,078 5/1978 Heim ...................................... 73/23

*Primary Examiner*—Stephen A. Kreitman
*Attorney, Agent, or Firm*—McGlew and Tuttle

[57] ABSTRACT

A method and apparatus of determining the alcohol content of the breath of a test person comprising, measuring the alcohol content of the breath to produce an alcohol content signal, measuring the change in the alcohol content signal, measuring a flow of the breath of the test person, and indicating the alcohol content using the alcohol content signal only when the change in the signal per unit time is below a preselected change value and the flow is above a preselected flow value and where the flow has not dropped below the predetermined flow value since it first reached the predetermined flow value. The change in the signal is determined by the change in the signal per unit time, times the inverse of the instantaneous value for the signal. When the change in the signal satisfies the requirement, a control signal is fed to an AND gate. When the flow value is reached, a second control signal is supplied to the AND gate through a first flip-flop circuit which is connected to a second flip-flop circuit so that no signal is applied to the AND gate if the flow value has dropped below the preselected flow value after it first reached the preselected flow value.

9 Claims, 2 Drawing Figures

METHOD FOR DETERMINING THE ALCOHOL CONTENT IN BREATHING AIR

FIELD AND BACKGROUND OF THE INVENTION

The present invention relates in general to alcohol concentration sensing apparatus and methods used to determine the alcohol content of a person's breath and in particular, to a new and useful method and apparatus for determining the alcohol content of a test person's breath by showing a signal representing the concentration only when the rate of change of the signal has dropped below a preselected value and where the flow of breath is maintained above a preselected value.

The U.S. Pat. No. 4,090,078 concerns a method and an arrangement for determining the alcohol content in breathing air of a test person with an alcoholometer which is exposed to the exhaling air and which transmits the determined value of the alcohol concentration in the form of a signal S(t) when the variation of S(t) per unit of time as related to the height of the alcohol signal S(t) is below a given threshold value $$W = \frac{1}{S(t)} \cdot \frac{dS}{dt};$$

and where the velocity of flow v of the exhaling air is above a given threshold value, and maintains this condition for a given time t without interruption. Methods and arrangements for measuring the alcohol content of the breathing air determine the real alcohol concentration when the portion of the exhaled air is tested for its alcohol value, that is, in equilibrium with the alcohol concentration of the blood in the alveoli of the lungs. The shuttle air from the oral and pharyingeal cavity and the mixed air from the alveolar air must therefore be measured separately.

According to the U.S. Pat. No. 4,090,078, the alveolar air portion is determined by monitoring the rise dS/dt of the alcohol concentration per unit time. This rise diminishes constantly with the alveolar air portion following the exhaled air from the oral and pharylingeal cavity until it stops completely when a concentration plateau is reached. When the rise, related to the instantaneous concentration, drops below the given threshold value w, only alveolar air is contained in the alcoholometer. Monitoring this rise in cooperative test persons would suffice to determine an alcohol concentration close to the value in the alveolar air. In practice, however, cooperation cannot always be expected. For this reason two additional conditions must be satisfied together with the monitoring of the rise before a measured value is indicated. The velocity of flow v determined by a flowmeter must be above a given value $v_{min}$ and must have been maintained for a given period of time.

A measuring instrument is used for the measurements with a short response time.

SUMMARY OF THE INVENTION

The subject matter of the present invention is a further development of the method and arrangement with the objective of permitting a more flexible adaptation of the measuring arrangement to the test person.

The essential advantages resulting from the further development of the U.S. Pat. No. 4,090,078 lie in the elimination of needing a given time interval.

If the rise conditions are satisfied before the time interval has expired, the test person must continue to blow until the end of the time interval with a given mean time interval t adapted to the test persons. Only then does a given time interval t make sense at all. Some of the test persons will be stressed more than necessary. Under certain circumstances, the conditions of the device may not even ever be satisfied.

The method and apparatus according to the invention adapts itself to the test person. Thus test persons with a below-average lung volume can be tested with this method.

Due to the absence of the time condition, the device adapts itself in practice to a wide spectrum of the test persons. There is no risk that test persons with a small lung volume will be overstressed by prolonged blowing. The test is completed when the variation per unit of time, related to the height of the alcohol signal, drops below the given threshold value.

Accordingly, an object of the present invention is to provide a method of determining the alcohol content of the breath of a test person comprising, measuring the alcohol content of the breath to produce an alcohol content signal, measuring the change in the alcohol content signal per unit time, measuring the flow of breath of a test person, and indicating the alcohol content using the alcohol content signal only when the change in the signal per unit time falls below a preselected change value and the flow rises above a preselected flow value and is maintained above the preselected flow value since the flow first reached the preselected flow value.

A further object of the present invention is to determine the rate of change of the signal per unit time by multiplying the inverse of the instantaneous value for the alcohol content signal by the rate of change of the alcohol signal per unit time.

A further object of the present invention is to provide an apparatus for determining alcohol content of a test person's breath comprising alcohol content measuring means for receiving the person's breath for converting the alcohol content of the breath into an alcohol content signal, a gate connected to the alcohol content measuring means for receiving the alcohol content signal, an indicator connected to the gate for indicating a value corresponding to the alcohol content signal only when the gate is activated, arithmetic means connected to the alcohol content measuring means for receiving the alcohol content signal and determining a rate of change per unit time of the signal, a comparator connected to the arithmetic means for receiving the rate of change value and comparing it to a predetermined rate of change value, an AND gate having one input connected to the comparator for receiving a signal when the rate of change of the alcohol content signal has fallen below the preselected change value and an output connected to the gate for activating the gate when the AND gate receives a signal at all its inputs, a flow meter for receiving the person's breath and sensing the flow thereof, a flow comparator connected to the flow meter for receiving a signal corresponding to the flow of breath and comparing the signal to a minimum flow value to produce a control signal which is connected to another input of the AND gate for activating the gate to indicate the value of the alcohol content signal.

A further object of the present invention is to provide an apparatus for determining the alcohol content of a test person's breath as defined above which further includes a first flip-flop connected to the control signal output of the flow comparator having an output connected to a further input of the AND gate, a second flip-flop connected to the output of the first flip-flop and having an output connected to the first flip-flop for deactivating the first flip-flop to disable the AND gate when the flow value falls below the preselected minimum value at any time after the flow value originally rose to the minimum flow value.

A still further object of the present invention is to provide an apparatus for determining the alcohol content of a test person's breath which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
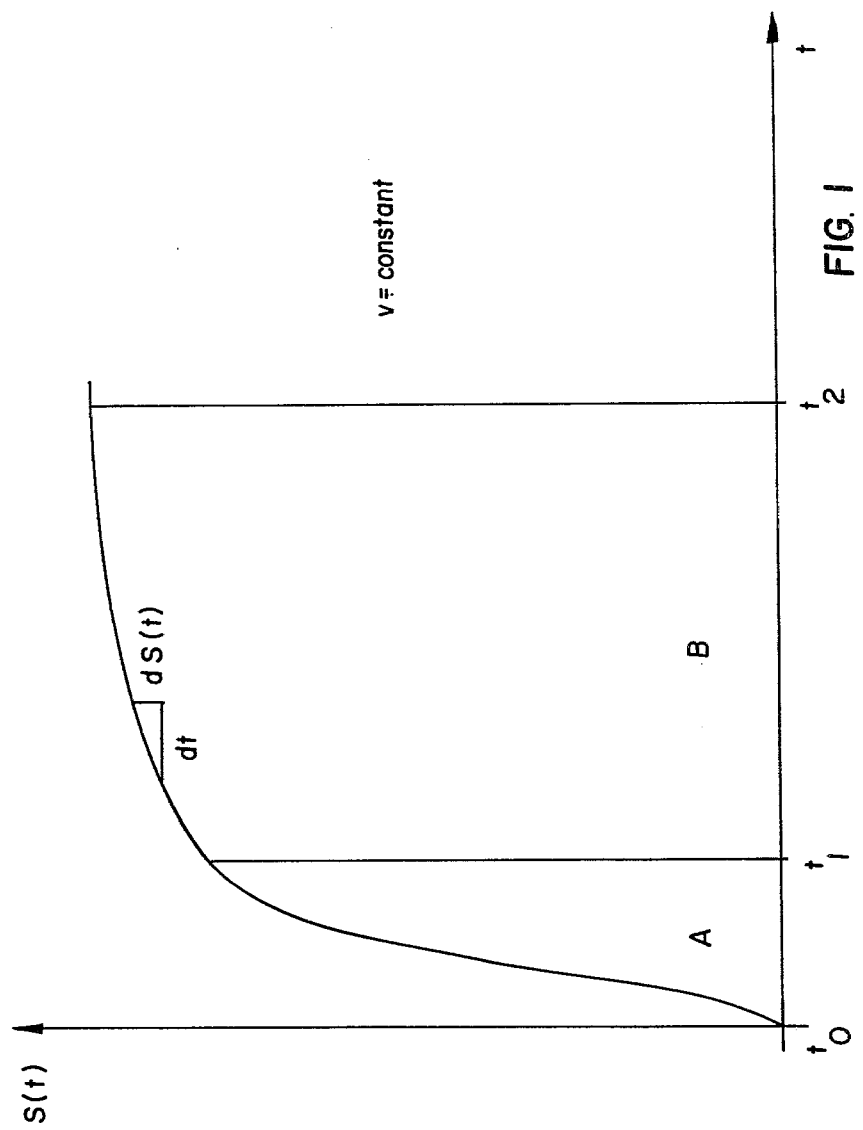
FIG. 1 is a graph showing an alcohol signal S(t) related to the time t.

In FIG. 1 the rise of the alcohol concentration in the breathing air per unit time is plotted with the signal S(t) on the ordinate and the time t on the abcissa. The curve shows two characteristic time periods A and B. In period A, with a measuring time phase $t_0-t_1$, a steady rise of the alcohol concentration can be observed. The shuttle air becomes more and more mixed with alveolar air from the lungs.

Period B, with a measuring time phase $t_1-t_2$ shows practically no further rise of the alcohol concentration. The curve moves toward a plateau. Only alveolar air is exhaled during this period.

Figure 2:
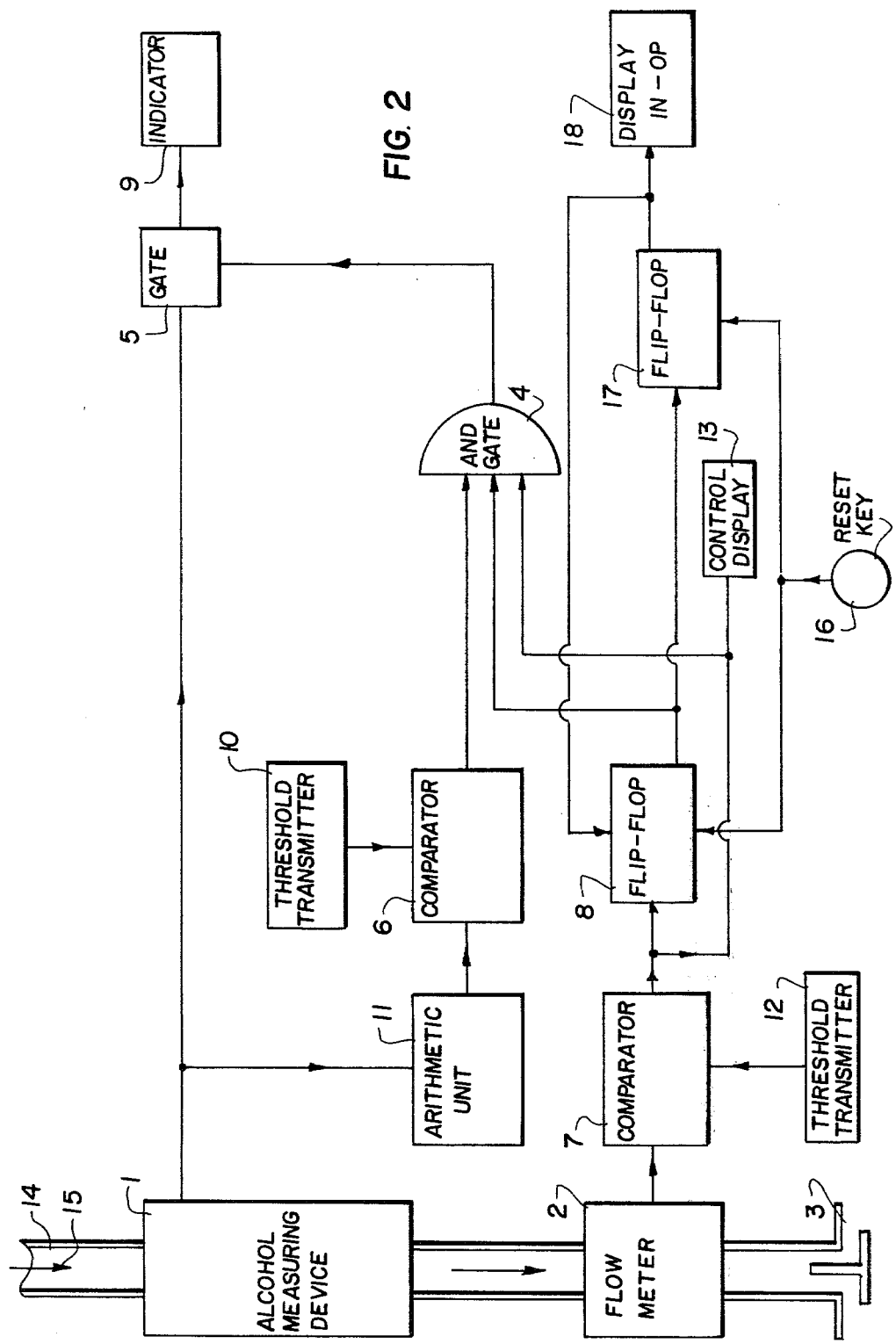
FIG. 2 is a schematic block diagram of an arrangement for measuring the alcohol content in the breathing air according to the invention.

Period B is clearly recognized by the arrangement according to the invention, as shown in FIG. 2. This recognition starts in the exhaling phase, when the value:

$$G = \frac{1}{S(t)} \cdot \frac{dS}{dt}$$

of the monitored rise, drops below the threshold value W. There is then practically no further rise of the alcohol value. In this period B, measuring instrument 1 measures the alcohol concentration of the breathing air which is in equilibrium with the blood. The construction of measuring instrument 1 corresponds to the state of the art. Measuring instrument 1 for measuring alcohol is connected into an exhaling air current carried by a tube 14. A nonreturn or one way valve 3 in tube 14 prevents a reversal of the exhaling air current flowing in direction 15. Following measuring instrument 1 is arranged a flowmeter 2 which measures the velocity of flow v. An AND gate 4 supplies a control voltage to linear gate 5 by which the alcohol signal S(t) is transmitted from measuring instrument 1 over linear gate 5 to indicating unit 9. Indicating unit 9 can be a recorder, a printer or a display storing the last, hence the maximum measured value.

A prerequisite for the issuance of a control voltage from AND gate 4 is that the two conditions a and b as defined below must be satisfied:

a: The quantity $G = \frac{1}{S(t)} \cdot \frac{dS}{dt}$;

where G is determined in the arithmetic unit 11 connected to the output of measuring instrument 1; must have dropped below the threshold value W. The threshold value W is fed-in by threshold transmitter 10 and compared with G in the first threshold comparator 6. With $G \leq W$ a control signal is sent to AND gate 4.

b: The velocity of flow v measured in flowmeter 2 must be greater than the minimum velocity of flow $v_{min}$ fed in by threshold transmitter 12 and must have been greater since $v_{min}$ was exceeded the first time. In this case a second threshold comparator 7 sends a control signal over first flip-flop 8 to AND gate 4. Flip-flops 8 and 17 react to the dropping edge of logic signals or pulses. If a positive signal (pulse) appears at the output of threshold comparator 7 at the velocity of flow $v_{min}$, flip-flop 8 does not react at first. At its inverted output is therefore a positive voltage. When condition a is satisfied at the same time, AND gate 4 switches. But when $v < v_{min}$, after $v > v_{min}$ has already been satisfied, flip flop 8 switches, and the logical level zero appears at the inverted output applied to AND gate 4. This causes flip-flop 17 to switch and to block flip-flop 8. Flip-flop 8 no longer reacts from a signal from comparator 7 no matter how often it may exceed or drop below $v_{min}$. This condition is indicated by display In-op 18.

A new test must be started but first flip-flops 8 and 17 must be returned to their original position by pressing reset key 16. In this arrangement, AND gate 4 is clocked even at the end of the test when the test person has stopped blowing after the conditions have been satisfied, so that no signal appears anymore in indicating unit 9 because of linear gate 5. It is therefore, advisable to design it as a recorder, printer or display storing the last or maximum measured value.

Conditions a and b ensure that only alcohol signal S(t) from the alveolar air can be fed to indicating unit 9.

Control display 13 is connected between threshold comparator 7 and AND gate 4. It lights up red when the velocity of flow is $v < v_{min}$ and green when $v > v_{min}$.

While a specific embodiment of the invention has been shown and described in detail to illustrate the application of the principles of the invention, it will be understood that the invention may be embodied otherwise without departing from such principles.

What is claimed is:

1. A method of determining the alcohol content of the breath of a test person comprising, measuring the alcohol content of the breath to produce an alcohol content signal, measuring the change per unit time of the alcohol content signal, measuring the flow of the breath of the test person, and indicating the alcohol content using the alcohol content system only when the change in the alcohol content signal per unit time falls below a preselected change value, and the flow is above a preselected flow value, and, once having reached the preselected flow value, the flow of breath has not fallen below the preselected flow value since the flow first reached the preselected flow value.

2. A method according to claim 1 wherein the measuring of the change of the alcohol content signal per unit time is produced by forming a value equal to the inverse of the instantaneous value for the alcohol content signal times the rate of change of the alcohol content signal per unit time.

3. A method according to claim 2 wherein the measuring of the alcohol content and of the flow of breath is accomplished from a single flow of the test person's breath which is provided through a tube having a one-way valve at the end thereof to prevent a reversal in the flow in the tube.

4. An apparatus for determining the alcohol content of the breath of a test person comprising, alcohol content measuring means adapted to receive the test person's breath and produce an alcohol content signal corresponding to the alcohol content of the person's breath, a control gate connected to said alcohol content measuring means for receiving the alcohol content signal, an indicator connected to said control gate for indicating a value corresponding to the alcohol content signal when said control gate is enabled, enabling means having at least two inputs and one control output connected to said control gate for enabling said control gate when said at least two inputs are enabled, signal change measuring means connected to said alcohol content means for receiving the alcohol content signal when comparing it to a preselected change value, said signal change measuring means connected to one of said enabling means inputs for enabling said one of said inputs when a change in the alcohol content signal per unit time falls below the preselected change value, a breath flow meter adapted to receive the breath of the test person for producing a flow signal, and flow signal comparator means connected to said flow meter for receiving said flow signal and connected to the other input of said enabling means for enabling said other input when the flow signal is maintained above a preselected minimum flow value, said flow signal comparator means comprises a flow signal comparator connected to said flow meter having one input connected to said other input of said enabling means, a minimum flow value transmitter connected to said flow comparator, a flip flop connected to the output of said flow comparator having an output connected to a further input of said enabling means, and a second flip-flop connected to an output of said former mentioned flip-flop having an output connected to an additional input of said first mentioned flip-flop for disabling said first mentioned flip-flop and providing a non-enabling signal to said additional input of said enabling means.

5. A device according to claim 4 wherein said signal change measuring means comprises an arithmatic unit for determining a value equal to the inverse of an instantaneous value for the alcohol content signal times the rate of change of the alcohol content signal per unit time, a comparator connected to said arithmatic unit and to said one of said enabling means inputs and a preselected change value transmitter connected to said comparator for supplying the preselected change value to said comparator.

6. A device according to claim 4 wherein said enabling means comprises and AND gate.

7. A device according to claim 4 further including reset means connected to said first mentioned and second flip-flops, a control display connected to the output of said comparator for indicating a flow signal above said minimum flow value and in-op display means connected to the output of said second flip-flop for displaying an inoperative condition for said first mentioned flip-flop.

8. A device according to claim 4 including a tube connected to said alcohol content measuring means and to said breath flow meter and a one-way valve connected to an output end of said tube for preventing a reverse flow of the breath in said tube.

9. A method of determining the alcohol content of the breath of a test person comprising, measuring the alcohol content of the breath to produce an alcohol content signal $S(t)$, measuring the change per unit time of the alcohol content signal $dS/dt$, measuring the flow of the breath of a test person, indicating the alcohol content using the alcohol content signal only when the value $1/S(t) \times dS/dt$ falls below a preselected value, and the flow is above a preselected value, and once having reached the preselected flow value, the flow of breath has not fallen below the preselected flow value since the flow first reached the preselected flow value.

* * * * *